United States Patent [19]

Murdock

[11] 4,239,487
[45] Dec. 16, 1980

[54] REMOVABLE ORTHODONTIC APPLIANCE

[75] Inventor: Dwight Murdock, Minneapolis, Minn.

[73] Assignee: Universal Dynamics, Inc., Minneapolis, Minn.

[21] Appl. No.: 59,267

[22] Filed: Jul. 20, 1979

[51] Int. Cl.³ .............................................. A61C 7/00
[52] U.S. Cl. ......................................................... 433/7
[58] Field of Search ........................................ 433/7, 6

[56] References Cited

U.S. PATENT DOCUMENTS

| | | | |
|---|---|---|---|
| 3,454,001 | 7/1969 | Stockfisch | 433/7 |
| 4,026,023 | 5/1977 | Fisher | 433/7 |

*Primary Examiner*—Robert Peshock
*Attorney, Agent, or Firm*—J. Michael Rosso

[57] ABSTRACT

A U-shaped acrylic body is separated at its closed end and slideably connected by means of a turnbuckle to allow lateral adjustment, the acrylic body further having a palatal wire extending into the palatal area of the mouth, buccal wires emerging from the outer sides and extending in a rectangular construction parallel thereto, and cuspid guidance wires emerging perpendicularly from the outer sides. The palatal wire is separated at its approximate midpoint in the palatal area and slideably connected, such that when the appliance is positioned in the mouth adjacent the inner sides of the teeth the wearer can make periodic lateral adjustments.

12 Claims, 9 Drawing Figures

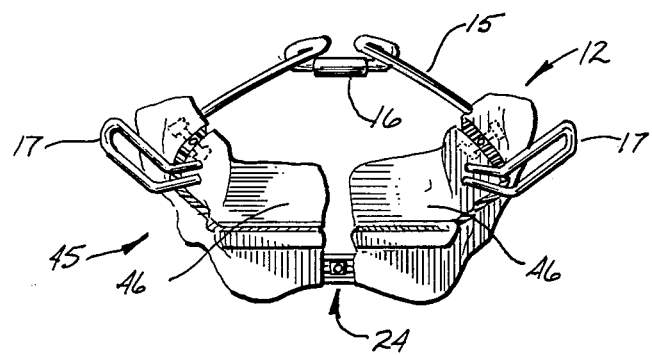
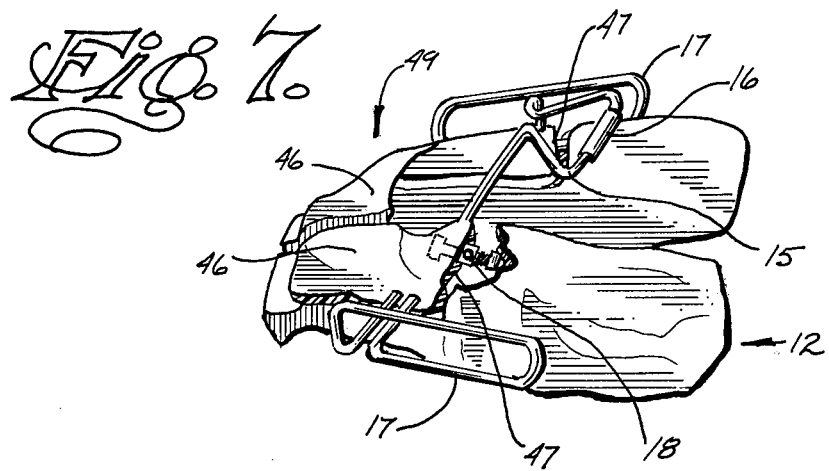
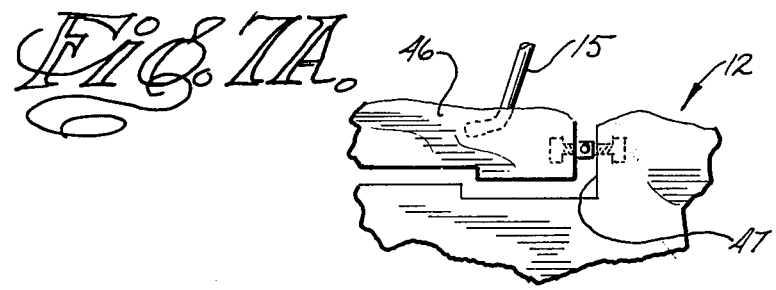

REMOVABLE ORTHODONTIC APPLIANCE

BACKGROUND OF THE INVENTION

This invention relates to orthodontic appliances and, more particularly, to a removable orthodontic appliance that can be periodically adjusted by the wearer.

Permanent or fixed appliances, such as braces, have long been used, especially with children, to correct dental abnormalities such as misalignment or crowding of teeth. Such appliances, although being excellent for controlling the direction of growth and spacing of teeth, have not been adapted for remedying malocclusions, such as overbite and overjet. Also, fixed appliances have proven to be a costly method for correction of dental abnormalities, and have been relatively unpopular with patients, due to adverse cosmetic and other characteristics.

More recently, removable appliances, with headgear apparatus, have been developed to remedy specific dental problems. One such construction, designed specifically to remedy the open mandibular posture, uses a thermoplastic horseshoe-shaped device which is inserted into the patient's mouth and attached to headgear for exerting an upward or vertical pull. Such constructions, with their highly visible headgear straps, have remained unpopular with patients. Additionally, they have only been adapted for use in limited problem areas, such as to remedy vertical abnormalities.

Another type of removable acrylic appliance, represented for example by the open end activator appliances, uses an acrylic body and labial and palatal wires to achieve correction of a wide variety of malocclusions. Despite their widespread use, and their applicability to numerous dental abnormalities, they have not been fully adequate in specific malocclusion cases, especially in overbite/overjet malocclusions, primarily because of their heavy weight and requirement for acrylic and other adjustments during their period of use. There has not been available a lightweight removable appliance which can be adjusted by the wearer, and which specifically corrects overbite/overjet and open bite problems.

SUMMARY OF THE INVENTION

In accordance with this invention there is provided a removable orthodontic appliance comprising a U-shaped plastic body adapted to fit within the mouth adjacent the inner sides of the upper and lower teeth, the plastic body being separated at the approximate midpoint of its closed end and being connected there by means which allows the two halves to be moved apart laterally. A palatal wire is attached to the sides of the plastic body, extends into the palatal area of the mouth, and is separated in such area and slideably connected to allow for self-adjustment in response to lateral movement of the two halves of the plastic body. A pair of buccal wires are attached to the outer sides of the plastic body, for abutting the outer sides of the teeth.

The means for connecting the two halves of the plastic body preferably comprises a turnbuckle set into the plastic and having a turning mechanism exposed in the separation, such that the wearer himself can turn the device to achieve periodic lateral movement of the two halves. Also, cuspid guidance wires, consisting of wire loops emerging perpendicularly from the outer sides of the plastic body, can be used to more accurately position the appliance.

It is a primary object of this invention to provide a lightweight removable orthodontic appliance that can be easily and quickly adjusted by the wearer.

It is another object of this invention to provide an orthodontic appliance for obtaining the most rapid correction of overbite, overjet and open bite malocclusions.

It is a further object of this invention to provide an orthodontic appliance which can be comfortably worn, even while speaking, and which achieves high patient acceptance.

BRIEF DESCRIPTION OF THE DRAWINGS

FIG. 6 is a front elevational view of a modified appliance; and

FIG. 7 is a side view, partially broken away, of the appliance shown in FIG. 6.

FIG. 7A is a fragmentary sectional view of the appliance shown in FIG. 7.

DESCRIPTION OF THE PREFERRED EMBODIMENTS

Figure 1:
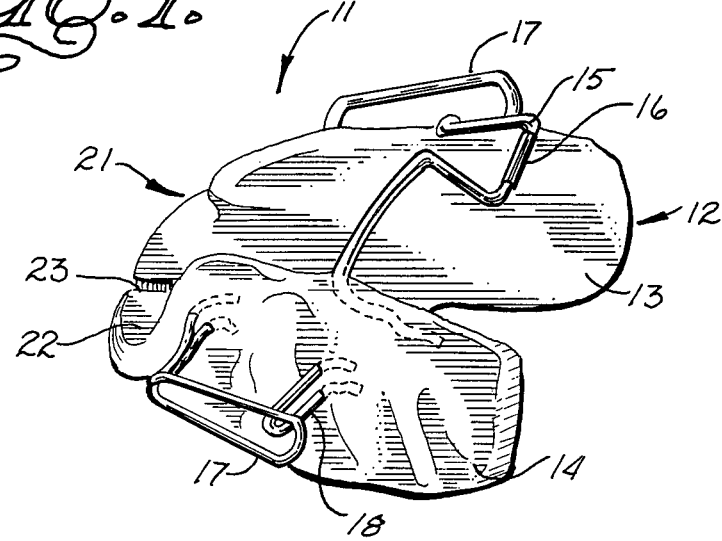
FIG. 1 is a perspective view of the orthodontic appliance of this invention.
Figure 2:
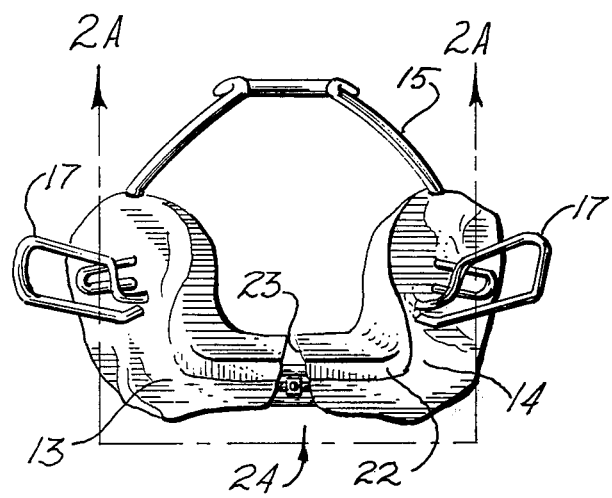
FIG. 2 is a front elevational view of the appliance shown in FIG. 1.
Figure 2A:
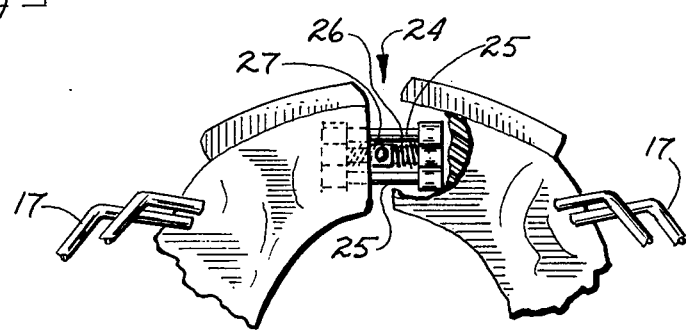
FIG. 2A is a fragmentary view showing the turnbuckle means connecting the two halves of the plastic body.
Figure 4:
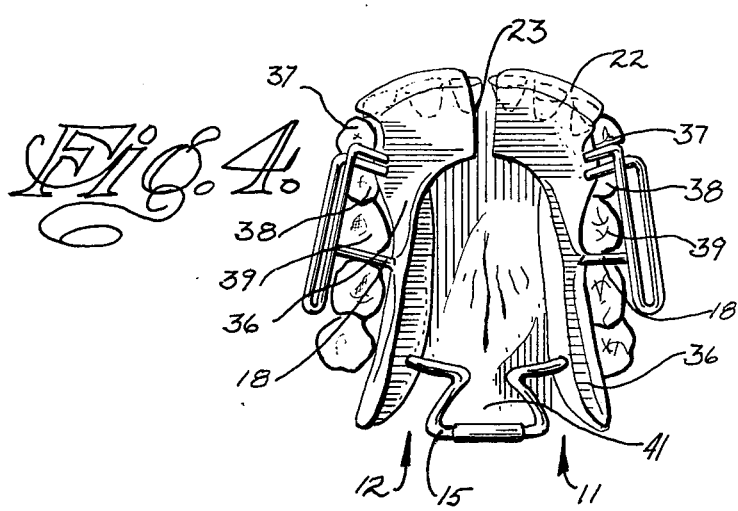
FIG. 4 is a view of the appliance of FIG. 1 shown in place on the maxilla.

Referring to FIG. 1, orthondontic appliance 11 has a U-shaped body portion 12 formed of two halves, 13, 14, joined together as is more clearly shown in FIGS. 2, 2A. Body portion 12 is formed of thermoplastic, preferably an acrylic, and is molded to fit within the mouth adjacent the insides of the upper and lower teeth. Palatal wire 15 extends from body portion 13 to portion 14, projecting into the palatal area of the mouth, where it is separated and slideably connected by cylindrical member 16. Buccal wires 17 emerge from the sides of plastic body 12 and extend parallel thereto in a rectangular construction. Cuspid guide wires 18 project perpendicularly from the sides of plastic body 12, and are used to assure an accurate fit, as shown in FIG. 4. Palatal wire 15, buccal wires 17 and guide wires 18 are attached to each plastic body half 13, 14 by embedding their ends in the plastic prior to curing.

The closed end 21 of plastic body 12 has an integral flange 22 projecting outwardly from the plastic body, with separation 23 dividing the body into halves 13, 14. Flange 22 abuts the upper and lower incisors when the appliance is in position within the mouth, as more clearly shown by FIG. 3.

Continuous separation 23, as shown in FIGS. 2, 2A, runs from the approximate midpoint of flange 22 rearwardly, the two halves 13, 14 of plastic body 12 being connected by turnbuckle 24. Palatal wire 15 and turnbuckle 24 firmly secure together the two halves 13, 14 to provide a rigid plastic and wire construction. Turnbuckle 24, which is embedded in the plastic body across separation 23, is formed of truss rods 25 and screw 26, having aperture 27. By inserting a pin into aperture 27, and turning screw 26, the halves 13, 14 can be moved apart laterally, the palatal wire 15 adjusting laterally by itself.

Figure 3:
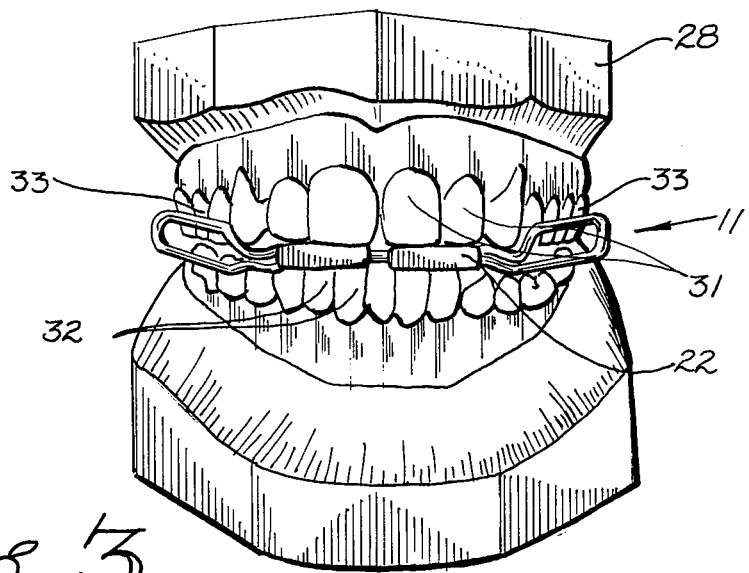
FIG. 3 is a front elevational view showing the appliance of FIG. 1 in position on a cast.

Referring to FIG. 3, appliance 11 is shown in position on cast 28, as it would be fitted into a patient's mouth. Flange 22 extends across the upper and lower incisors 31, 32, to provide full incisal contact. This assures proper alignment of upper and lower dental arches, and thereby eliminates misalignment problems, such as "scissors" bite. Buccal wires 17 abut the upper and lower premolars 33, 34, and on their outer sides engage the patient's cheek muscles and use the force of such muscles to achieve proper growth of the bony structure of the jaw. The combination of full incisal contact and engagement of the cheek muscles has been found to provide unusually rapid correction of dental abnormalities.

As shown in FIG. 4, appliance 11 fits within the patient's mouth in contact with the inner sides of the teeth, the upper arch being shown. The two halves 13, 14 of plastic body 12 are molded to fit snugly against the teeth and portion of the gums, the outer sides 36 being grooved for such purpose. Buccal wires 17 emerge between the canine teeth 37 and the first premolars 38, and cuspid guide wires 18 emerge after the second premolars 39, to provide firm fitting of the appliance. Palatal wire 15 contacts the palatal area 41 of the patient's mouth. The flange 22, separated at 23, extends from plastic body 12 to cover incisors 31, 32.

Figure 5:
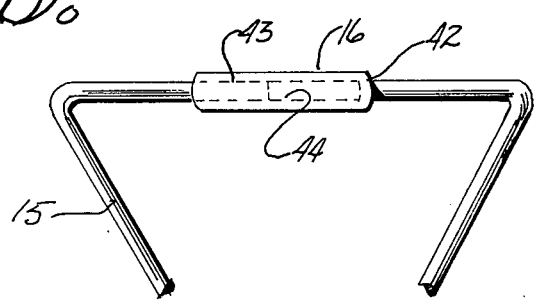
FIG. 5 is an enlarged fragmentary view showing the slideable connection of the palatal wire.

FIG. 5 shows in enlarged view the self-adjusting palatal wire 15, with cylindrical connecting member 16. Palatal wire 15 is separated within cylindrical member 16, which is attached to free end 42. The outer free end 43 can move within passage 44 to allow for lateral movement of the appliance when turnbuckle 24 is operated. Palatal wire 15 is thereby completely self-adjusting, and needs no attention from the patient.

FIGS. 6, 7 and 7A show a modified appliance 45 for use specifically in case of crowded maxillary incisors. In addition to plastic body 12, buccal wires 17, palatal wire 15, cylindrical connector 16 and turnbuckle 24, appliance 45 has integral portions 46 on the upper arch sections thereof. This construction allows treatment of the crowding problem at the same time that repositioning of the mandible is taking place in response to the muscular pattern set by the appliance.

Appliance 45 can also be provided with vertical separations 47 on each side of the plastic body 12, and turnbuckles 48 to allow sagittal adjustment of the appliance. That is, portions 46 can be moved forward, in the direction of the arrow. Cuspid guide wires, as shown in the above figures, are also preferably used, to assure optimum positioning of the appliance within the patient's mouth. Appliance 45 effectively eliminates the need for a series of appliances, thereby remedying crowding and dental abnormalities in the shortest possible time.

Further modifications of the plastic body 12 of the appliance of this invention can be made, depending on the specific dental problem sought to be solved. Usually this will require the addition of more plastic to the body portion, as in the appliance shown by FIGS. 6, 7 and 7A. For example, for open bite problems, the plastic body can be built up to prevent the tongue from thrusting between the teeth. However, one of the primary advantages of the appliance of this invention is that it is of extremely light weight compared to other removable appliances. This means that the appliance will be much less visible, leading to better patient acceptance. Further, speaking will be easier for the patient, with the appliance in place. Also, the appliance is more comfortable than heavier and bulkier appliances.

The appliances of this invention are positioned by loosely fitting them into the patient's mouth, with the guide wires and buccal wires helping to properly locate them. The patient then bites down, using the muscles of mastication to hold the appliance in place. It is the use of such muscles that brings about, over a period of months, the change in internal bone structure of the jaw necessary to correct dental abnormalities. That is, the appliances correct malocclusions by changing the functional pattern of the muscles of mastication, primarily the masseter and the lateral pterygoid muscles. The appliance is constructed so as to bring the mandible into slight overcorrection in relation to the maxilla, to achieve this change in muscle pattern. Growth will then take place in the boney structure of the jaw, such as in the alveolar bone, resulting finally in a permanent and stable dental structure.

The most rapid results are obtained when the patient's incisors are brought into end to end relationship by the appliance, with a spacing of about 2 mm between the incisors. Also, a labial bow can be added to the appliance, provided it is of the extended type and used together with the buccal wires as shown.

A significant advantage of the appliance of this invention is the absence of any need for adjustment by the dentist or dental laboratory during the treatment. There is no need for any modification of the plastic during treatment. The patient can operate the turnbuckle, a quarter turn or so every week, to allow the plastic body to expand laterally as the patient grows. Accordingly, the appliance provides an optimum remedy for the quickest possible resolution of malocclusions, and one which has high patient acceptance due to its compact structure.

It is claimed:

1. An orthodontic appliance comprising
   (a) a U-shaped plastic body adapted to fit within the mouth adjacent the inner sides of the upper and lower teeth, the closed end being adjacent the front teeth and being separated at the approximate midpoint to divide the plastic body into slightly spaced apart matching halves;
   (b) means disposed across the separation of the closed end of the plastic body for connecting the two halves and allowing each half to be moved apart laterally;
   (c) a palatal wire connected across the sides of the plastic body and adapted to extend into the palatal area and towards the rear of the mouth, the wire being separated at its approximate midpoint;
   (d) means for slideably connecting the free ends of the palatal wire for allowing lateral movement thereof; and
   (e) a pair of buccal wires, each attached to an outer side of the plastic body, the wires adapted to abut the teeth on the outer sides thereof.

2. The orthodontic appliance of claim 1 additionally comprising a pair of wire loops extending perpendicularly from the sides of the plastic body out to the area of the buccal wires, for cuspid positioning of the appliance.

3. The orthodontic appliance of claim 1 wherein the means connecting the two halves of the plastic body comprises a turnbuckle set into the plastic and having a metal pin with an aperture exposed between the separation, for lateral adjustment by the wearer.

4. The orthodontic appliance of claim 1 wherein the means for slideably connecting the free ends of the palatal wire comprises a cylindrical metal member attached to one free end and being adapted to snugly receive the other free end.

5. The orthodontic appliance of claim 1 wherein each buccal wire comprises a single wire emerging from the front portion of the plastic body and running along the side thereof in a substantially rectangular construction back to the point of emergence.

6. The orthodontic appliance of claim 1 wherein the closed end of the plastic body has a flange which projects between the wearer's incisors and contacts the upper and lower incisors after biting down.

7. The orthodontic appliance of claim 1 wherein the plastic body is formed of acrylic.

8. The orthodontic appliance of claim 1 wherein the buccal wires fit between the canine and premolar teeth on either side of the wear's jaw, and wherein the wire loops fit behind the second premolars.

9. The orthodontic appliance of claim 1 wherein the inner sides of the plastic body have grooves accomodating adjacent upper and lower teeth.

10. The orthodontic appliance of claim 1 additionally comprising integral plastic panels running across the front of the appliance from either side thereof and from the closed end of the plastic body.

11. The orthodontic appliance of claim 10 wherein each of the sides of the plastic body are separated and slideably connected, to allow front to rear adjustment of the appliance.

12. The orthodontic appliance of claim 1 wherein the closed end of the plastic body has an upward projecting portion for preventing the tongue from thrusting between the teeth, to remedy open bite malocclusions.

* * * * *